United States Patent [19]

Schoenwald et al.

[11] Patent Number: 5,095,026

[45] Date of Patent: Mar. 10, 1992

[54] PRODRUGS OF CARBONIC ANHYDRASE INHIBITORS

[75] Inventors: Ronald D. Schoenwald; Charles F. Barfknecht, both of Iowa City, Iowa

[73] Assignee: University of Iowa Research Foundation, Iowa City, Iowa

[21] Appl. No.: 410,982

[22] Filed: Sep. 22, 1989

Related U.S. Application Data

[63] Continuation-in-part of Ser. No. 464,063, Feb. 4, 1983, Pat. No. 4,975,449.

[51] Int. Cl.$^5$ .............................................. A61K 31/425
[52] U.S. Cl. ..................... 514/367; 536/4.1; 536/1.1; 514/913; 514/54; 514/363; 514/603; 514/604
[58] Field of Search ................. 536/1.1, 4.1; 514/367, 514/913; 424/80, 270, 321

[56] References Cited

U.S. PATENT DOCUMENTS

| | | | |
|---|---|---|---|
| 4,386,098 | 5/1983 | Woltersdorf, Jr. et al. | 424/270 |
| 4,483,864 | 11/1984 | Barfknecht et al. | 424/270 |
| 4,483,872 | 11/1984 | Barfknecht et al. | 424/321 |
| 4,499,103 | 2/1985 | de Solms | 514/365 |
| 4,505,923 | 3/1985 | Hoffman, Jr. et al. | 514/229 |
| 4,510,155 | 4/1985 | Smith et al. | 514/367 |
| 4,629,738 | 12/1986 | Barfknecht et al. | 514/603 |
| 4,636,515 | 1/1987 | Barfknecht et al. | 514/363 |
| 4,861,760 | 8/1989 | Mazuel et al. | 536/1.1 |

OTHER PUBLICATIONS

Larsen et al., "Prodrug Forms for the Sulfonamide Group", Acta Pharm. Nordica 1, 31 (1989).
Bundgaard et al., "N-Sulfonyl Imidates as a Novel Prodrug Form for an Ester Function or a Sulfonamide Group", *J. Med. Chem*, 31, 2066 (1988).

*Primary Examiner*—Ronald W. Griffin
*Assistant Examiner*—Louise Leary
*Attorney, Agent, or Firm*—Zarley, McKee, Thomte, Voorhees & Sease

[57] ABSTRACT

Prodrugs are prepared of the carbonic anhydrase inhibitors 2-benzothiazolesulfonamide, hydroxymethazolamide, and dichlorphenamide. The prodrugs link a water soluble compound to the pharmacologically active carbonic anhydrase inhibitor through an enzymatically or hydrolytically degradable bond.

24 Claims, No Drawings

PRODRUGS OF CARBONIC ANHYDRASE CROSS-REFERENCE TO A RELATED APPLICATION

This application is a continuation-in-part of co-pending and commonly owned application Ser. No. 464,063 filed Feb. 4, 1983, now U.S. Pat. No. 4,975,449, and entitled TOPICAL TREATMENT FOR GLAUCOMA.

BACKGROUND OF THE INVENTION

Glaucoma, which some estimate affects 2 million adults over 40, is an impairment of vision caused by too much fluid pressure within the eye.

Surgical treatment for glaucoma is effective; however, it is expensive and some surgeons will use surgery only as a last resort.

Carbonic anhydrase inhibitors, prescribed orally, work well to treat this disease, but they carry a host of side effects, from nausea to kidney stones.

Glaucoma stems from an excess of fluid behind the cornea, the three-layered tissue that acts as a window to let light enter. Fluid carrying nutrients such as potassium and glucose constantly wash the inside of the cornea to keep it healthy much as tears wash the outside of the cornea.

In some middle-aged adults, fluids build up faster than can be absorbed back into the blood, for one of two reasons: the ciliary body (a tiny tissue behind the iris) may excrete too much fluid, or the fluid may not drain off at the normal rate.

Either way, the excess fluid damages the optic nerve. At first a glaucoma victim usually experiences a subtle loss of peripheral vision—objects will seem to disappear from certain spots to the side. But glaucoma often leads to middle-age blindness.

Unfortunately, the two approaches to general drug usage in treating glaucoma—topical (dropped into the eye) and oral—each have a peculiar set of side effects.

To make the long journey, oral drugs must be dosed in very high concentration. One class of drugs, called carbonic anhydrase inhibitors, slow the formation of fluid by inhibiting a chemical reaction at the ciliary body. Along with their well-tested effectiveness comes nausea, tingling in fingers and toes, and other side effects. Oral drugs generally do not, however, cause side effects in the eye.

Certain topical drugs, while causing less systemic effects, on the other hand, can cause severe headaches and constrict the pupil, making the daytime appear dark.

In our parent application, analogs of 2-benzothiazolesulfonamides are prepared as carbonic anhydrase inhibitors. While many of the compounds that are prepared are carbonic anhydrase active, in fact some have limited practical usage because the compounds are poorly soluble in water. This is not only true for certain carbonic anhydrase inhibitor active 2-benzothiazolesulfonamides, but it is also true for certain other carbonic anhydrase inhibitors such as methazolamide/acetazolamide analogs and dichlorphenamide analogs.

Compounds which are carbonic anhydrase active inhibitors but have limited solubility in tears are, as a practical matter, of limited value in developing topical carbonic anhydrase inhibitors. Put another way, if the compound will not dissolve in the tears, its chances of penetrating the cornea to release the pharmacologically active carbonic anhydrase inhibitor are small, at best. Thus, it is important if one is developing effective carbonic anhydrase inhibitors which can be topically applied, that the compound be soluble in water and tears.

It is a primary objective of the present invention to provide carbonic anhydrase inhibitors with enhanced water solubility without negatively impacting their carbonic anhydrase activity.

It is another objective of the present invention to prepare prodrugs of certain carbonic anhydrase inhibitors, in particular, 2-benzothiazolesulfonamides, methazolamide/acetazolamide and dichlorphenamide. The prodrugs have a high degree of solubility in tears, and can effectively penetrate the cornea and release the pharmacologically active carbonic anhydrase inhibitor by enzymatic and/or hydrolytic degradation of a chemical bond between a water soluble moiety and the carbonic anhydrase inhibitor.

An even further objective of the present invention is to prepare and use as topical carbonic anhydrase inhibitors certain novel compounds derived from carbonic anhydrase inhibitors by chemically bonding a water soluble carrier to a carbonic anhydrase inhibitor through a bond which is enzymatically cleavable.

The method and manner of accomplishing each of the above objectives as well as others will become apparent from the detailed description of the invention which follows hereinafter.

SUMMARY OF THE INVENTION

Water soluble prodrugs of carbonic anhydrase inhibitors are prepared by linking a water soluble moiety to the carbonic anhydrase inhibitor, through a chemical bond which can be enzymatically or hydrolytically cleaved in the eye. As a result, the increased water solubility allows improved topical administration and the cleaving of the bond allows the carbonic anhydrase inhibitor to then function to reduce intraocular pressure.

DETAILED DESCRIPTION OF THE INVENTION

Inhibition of carbonic anhydrase is one mechanism of action by which the production of aqueous humor can be limited within the eye If aqueous humor production can be limited, this in turn can be used to control ocular hypertension. Carbonic anhydrase inhibitors can be administered orally to reduce intraocular pressure (IOP), but this route of administration is associated with systemic side effects due to the large doses required to attain therapeutically useful levels in the eye. Topical administration of carbonic anhydrase inhibitors directly to the eye has the advantage of minimizing or eliminating systemic side effects due to the smaller doses required, and the more direct access the drug has to the organ. However, a carbonic anhydrase inhibitor may not produce optimum therapeutic effects, and may not be adequately absorbed or distributed to the active site, or may cause ocular irritation or local side effects as a result of changes in the carbonic anhydrase inhibitor molecule necessary to achieve water solubility. Thus, in preparing carbonic anhydrase inhibitors, one must constantly balance the activity, that is the effectiveness at inhibiting carbonic anhydrase, against the local or side effects that may be caused by changes necessary in the molecule in order to make it water soluble. For example, many carbonic anhydrase inhibitors that have been patented in the past achieve water solubility due to the presence of a tertiary amine which is protonated at physiological pH. In this situation, the less than optimal water solubility of the active carbonic anhydrase inhibitor is accompanied by enhanced lipophilic solubility which translates into greater penetration to the site of action. However, if optimal water solubility were obtained by protonation to the active carbonic anhydrase inhibitor, one would necessarily be faced with less lipophilic character and accordingly a decreased amount of drug reaching the site of action, due to the more difficult penetration of the cornea. The net result would be a less clinically effective agent.

In accordance with the present invention, it has been discovered how certain prodrugs of three distinct classes of carbonic anhydrase inhibitors can be made more water soluble for dissolving in the tears by attachment of water soluble moieties through linkages which can be degraded to the active carbonic anhydrase inhibitor which has greater lipophilic solubility for penetration and accumulation at the site of the action. In short, the optimal water solubility in the tears of the prodrug is achieved without protonation, and later, when converted to the active carbonic anhydrase inhibitor within the eye, optimum lipid solubility in the tissue is achieved. As a result, one combines both desirable properties.

The carbonic anhydrase inhibitors which can be used to make the prodrugs of this invention, and which have both a high degree of water solubility and a high degree of penetrability of the cornea so that maximum effective delivery of the active carbonic anhydrase inhibitor is achieved, include 2-benzothiazolesulfonamides of the structure:

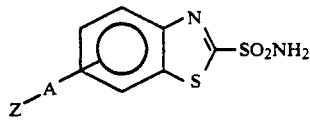

Another class of carbonic anhydrase inhibitors which can be utilized in this invention are hydroxymethazolamides of the formula:

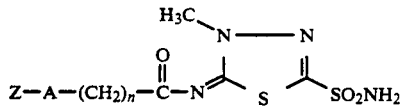

A third class of carbonic anhydrase inhibitors are dichlorphenamide analogs of the formula:

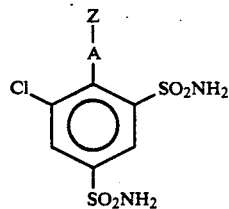

In each of the general formulas given for 2-benzothiazolesulfonamides, the hydroxymethazolamides and dichlorphenamides, the "Z" represents a water soluble carrier and "A" is a moiety which is attached to the carbonic anhydrase inhibitor which allows it to still retain carbonic anhydrase inhibitory activity, but also form an enzymatically cleavable bond between A and Z.

As used herein, "enzymatically cleavable bond" refers to a bond which can be cleaved after the compound is dropped onto the eye. The cleavage can be by enzymatic cleavage and/or hydrolytic cleavage. As a result, the water soluble compound is formed by covalently linking a pharmacologically active, but insufficiently water soluble, carbonic anhydrase inhibitor to a water soluble carrier, Z, through an enzymatically and/or hydrolytically degradable bond, "A". The water soluble prodrug dissolves in the tears, penetrates and degrades within the cornea to release the pharmacologically active carbonic anhydrase inhibitor which distributes and accumulates in the ciliary body, inhibits the enzyme carbonic anhydrase with a resulting decrease in the production of aqueous humor. Thus, intraocular pressure is reduced.

Key aspects of this invention are: First, synthesis of a molecule which inhibits carbonic anhydrase and has less than optimum water solubility itself, but which does contain a functional group which can be covalently linked through "A" to the water soluble carrier. Secondly, the linkage of the "carbonic anhydrase inhibitor-A" to a water soluble carrier by a covalent bond such as an ester, carbamate, carbonate, glycoside, etc. which can be degraded by enzymes present in the eye and/or hydrolyzed at physiological pH. Third, the water soluble carrier Z must attain its solubility due to the presence of two or more hydroxyl groups, and without the presence of groups which are ionized at physiological pH. Thus, the water soluble carrier should not be a surface active agent or pharmacologically active itself.

Typical compounds which may be used as the water soluble carriers, Z, include monosaccharides such as D- and L-glucose, 6-carboxylic acid derivatives of monosaccharides such as D- and L-glucuronic acid, and D- and L-gluconic acid, and the like.

Suitable moieties represented by A include hydroxyalkoxy, preferably $C_1$ to $C_5$ alkyl, and most preferably alkoxyethoxy, simple hydroxy, hydroxy acetamido, and amine.

Where the water soluble non-ionizable carrier, Z, is a monosaccharide or a 6-carboxylic acid derivative of monosaccharides, it is preferred that A be hydroxyethoxy.

The linkage or covalent bond between Z and the carbonic anhydrase inhibitor ring system can be described as a covalent, degradable linkage between the active carbonic anhydrase inhibitor molecule and the water soluble carrier. This linkage can be an ester linkage, a glycosidic linkage, a carbonate linkage, a carbamate linkage, a thiocarbamate linkage, a urea linkage, a thiourea linkage, etc. Preferably, where Z is a monosaccharide the linkage is glycosidic and where Z is a 6-carboxylic acid derivative of a monosaccharide, the linkage is esteratic, i.e. through the carboxylic acid.

These compounds are water soluble, have greater than 0.25% solubility on a weight/volume basis without significant contributions from ionization at physiological pH. Also, the carbonic anhydrase inhibitor is a potent inhibitor of the enzyme carbonic anhydrase, and does have significant water solubility in comparison with the compound prior to attachment of the water soluble carrier Z. Also, the linkage between Z and A can be degraded by enzymes present in the eye such as acetylcholinesterase, serum cholinesterase, glycolase, etc., or can be degraded by hydrolysis/decomposition at physiological pH to release the active carbonic anhydrase inhibitor.

Examples of active benzothiazole-2-sulfonamides which can be used in this invention are from the illustrative list in the parent application, Ser/ No. 464,063 filed Feb. 4, 1983, and are incorporated herein by reference.

Examples of methazolamide or N-[5-(aminosulfonyl)-3-methyl-1,3,4-triadiazol-2(3H)-ylidene]acetamide and its analogs which can be used are the following: hydroxymethazolamide, N-[5-(aminosulfonyl)-3-methyl-1,3,4-triadiazol-2(3H)-ylidene]hydroxyacetamide and hydroxyethoxymethazolamide, N-[5-(aminosulfonyl)-3-methyl1,3,4-triadiazol-2(3H)-ylidene]hydroxyethoxyacetamide. Other compounds modified from the parent molecule methazolamide and acetazolamide may also be prepared.

Examples of dichlorphenamide or 4,5-dichloro-m-benzenedisulfonamide which may be made and used are the following:
4-hydroxy-5-chloro-m-benzenedisulfonamide
4-hydroxyethoxy-5-chloro-m-benzenedisulfonamide
4-hydroxyacetamido-5-chloro-m-benzenedisulfonamide
4-hydroxyethoxyacetamido-5-chloro-m-benzenedisulfonamide.
Other 4-amino-6-chloro-m-benzenedisulfonamides; 4-hydroxyacetamido-6-chloro-m-benzenedisulfonamides; 4-hydroxy-6-chloro-m-benzenedisulfonamides; 4-hydroxyethoxy-6-chloro-m-benzenedisulfonamides; 4-chloro-5-hydroxy-m-benzenedisulfonamides; 4-chloro-5-hydroxyethoxy-m-benzenedisulfonamides; 4-amino-5-chloro-m-benzenedisulfonamides; 4-chloro-5-amino-m-benzenedisulfonamides; 4-hydroxyacemido-5-chloro-m-benzenedisulfonamides; and 4-chloro-5-hydroxyacemido-m-benzenedisulfonamides may also be used.

The water soluble moiety may be attached to the remaining portion of the molecule through linkages from two or more hydroxyl groups on the water soluble area of molecule Z by using known chemistry and simple addition reactions. In particular, the water soluble carrier Z with all hydroxyl groups protected except the site of reaction with A is reacted under appropriate reaction conditions with the carbonic anhydrase inhibitor analog to form the protected CAI prodrug. In the final step the protecting groups on Z are removed to form the water soluble prodrug. A general structure of the prodrug is as follows:

Z—A—Ring System—SO$_2$NH$_2$

An analog of one of the prototype carbonic anhydrase inhibitors (Ethoxzolamide, Methazolamide, Acetazolamide, or Dichlorphenamide) is designed and synthesized by either total synthesis or by conversion from a commercially available intermediate. The analog is characterized by its carbonic anhydrase inhibitory activity and the presence of a functional group (A). In general A will contain a terminal hydroxyl or amino group with or without other atoms) that will be covalently linked to the water soluble carrier Z through a linkage degradable at physiological pH and/or in the presence of normal ocular enzymes.

In order to obtain the specific linkage between Z and A, all functional groups on Z must be protected before reaction with the CAI analog except the group at the site of attachment. The reaction between protected Z and A to form the linkage (e.g., glycosidic (acetal), ester, carbamate, etc.) will occur under a variety of reaction conditions (in a solvent system, with or without additional reagents, with heating or cooling or at room temperature as appropriate for the chemical reaction) depending on the nature of Z, A, and the desired linkage between them. While linking Z to A can occur without interference from the sulfonamide group, sometimes it may be necessary to protect the sulfonamide group from unwanted reaction (just as one protects the other functional groups in Z) during the linkage formation and then deprotect the sulfonamide later. Likewise, the protected functional groups on Z (generally hydroxyl groups) must be deprotected after the linkage is formed between Z and A. This deprotection reaction must be selective in order not to disrupt the Z to A linkage, hydrolyze the sulfonamide group, or alter other parts of the prodrug.

The following examples are offered to further illustrate but not limit the process of this invention.

EXAMPLE 1

Synthesis of 6-[β-glucopyranosyl)oxyethoxy]-2-benzothiazolesulfonamide

A solution of acetobromoglucose (4.93 g.; 12.0 mmole), 6-[2'-hydroxyethoxy]-2-benzothiazolesulfonamide (2.74 g.; 10.0 mmole), and 2,4,6-collidine (1.09 g.; 9.00 mmole) in dry tetrahydrofuran (50 mL) were added at −25° C. to a suspension of silver triflate (3.60 g.; 14.0 mmole) in dry tetrahydrofuran over a period of 30 minutes. The reaction mixture was stirred overnight at room temperature. Collidine (2 mL) was added and the mixture filtered through paper. The filtrate was washed with aqueous sodium thiosulfate solution, the organic layer separated, and evaporated to dryness at reduced pressure. The solid residue was chromatographed on a silica gel column (300 g.) and eluted with chloroform. The product fractions (UV light and charring positive) were combined and evaporated to dryness at reduced pressure.

The unpurified 6-[2'-(2″,3″,4″,6″-tetra-O-acetyl-β-glucopyranosyl)oxyethoxy]-2-benzothiazolesulfonamide (3.02 g.; 5.00 mmole) was dissolved in anhydrous diethyl ether (100 mL) and combined with cold (0° C.) saturated methanolic ammonia (100 mL) and stirred overnight with the temperature rising to room temperature over a six hour period. The solution was evaporated to dryness at reduced pressure and chromatographed on a silica gel column (150 g.) and eluted with chloroform/methanol (9.1). The product fractions (UV light and charring positive) were combined and evaporated to dryness at reduced pressure, and lyophilized to yield 6-[β-lucopyranosyl)oxyethoxy]-2-benzothiazolesulfonamide. The product conformed to accepted standards of purity and its structural assignment verified by standard spectroscopic methods (mass spec, $^{13}$C and $^1$H nuclear magnetic resonance).

EXAMPLE 2

Reduction in IOP Following Topical Application of the Compound of Example 1 to Dutch Belt Rabbit Eyes Healthy, Dutch Belt rabbits, accustomed to the experimental procedure, 2-3 months old, of either sex and weighing about 3-4 pounds were placed in restraining boxes. Intraocular pressure (IOP) was measured using a pneumatonograph (Digilabs Model 30D, Cambridge, Mass.) and 1-2 drops of 0.5% proparacaine hydrochloride for anesthesia. IOP is measured in both eyes. The drug of Example 1 is dissolved in a 3% carbomer 940 vehicle (Carbopol 940, B. F. Goodrich, Cleveland, Ohio) and instilled (50 μL) into the lower conjunctival sac of the right eye only.

The "IOP recovery rate assay" as reported by Vareilles and Lotti (Ophthalmic Res., 13, 72-79, 1981) is used. In this assay 20% sodium chloride solution is infused into the marginal ear vein for 10 minutes at a rate of 1 mL/min. This procedure was altered by infusing 10% sodium chloride solution for 15 minutes at a rate of 1 mL/min. to minimize vascular damage IOP is measured just prior to beginning the infusion and again at 15, 25, 35, 45, 60, 75, 90, 120, 150, 180, and 210 minutes.

The hypertonic sodium chloride solution causes a decline in IOP which then recovers at a rate dependent on the activity of carbonic anhydrase. IOP gradually returns to normal at a constant rate but much more slowly if a carbonic anhydrase inhibitor is present in the eye in sufficient concentration. The return to normal is measured from the positive linear slope which begins at about 45-60 minutes after starting the infusion. The test drug (3% drug in carbomer vehicle) is administered 60 minutes before the start of the sodium chloride solution infusion. Control animals are given vehicle without drug.

Results are expressed as mean values ± standard deviation of the slopes representing recovery of IOP (mm Hg/min.):

| treated rabbits [n = 4 eyes] | control eyes [n = 2 eyes] |
|---|---|
| 0.068 ± 0.032 | 0.112 ± 0.0073 |

The topically treated rabbit eyes show a statistically slower (p<0.05) recovery rate to normal IOP values when compared to control eyes which only received vehicle. This indicates the drug works.

Other satisfactory results can also be achieved when the 2-benzothiazolesulfonamide carbonic anhydrase inhibitor of the Examples 1 and 2 is substituted with methazolamide/acetazolamide analogs and dichlorphenamide analogs, in that water solubility is increased, and carbonic anhydrase inhibition is still maintained at effective levels. This indicates degradation of the linkage between the water soluble carrier and the carbonic anhydrase inhibitor by enzymes within the eye such that the carbonic anhydrase inhibitor continues to exhibit CAI activity.

In these and other examples, as in the parent case, the amount of the carbonic anhydrase inhibitor active used in the composition should be from about 0.25% by weight to about 5% by weight of an eye drop test composition, preferably from about 0.5% by weight to about 2.0% by weight. The important point is not the dose amount, but simply that it be an effective carbonic anhydrase inhibiting amount, and yet not such a great amount that side effects will be achieved. Generally, amounts within the range specified are satisfactory.

The diluent for the eye drop composition may be an isotonic eye treatment carrier buffered to a pH of from about 4.0 to about 8.0, and typically it will contain small amounts of conventional wetting agents and antibacterial agents. The preferred pH is within the range of from about 6.8 to about 7.8. Antibacterial agents, where they are included may be within the range of from about 0.004% by weight to about 0.02% by weight of the composition.

What is claimed is:

1. Prodrugs of 2-benzothiazolesulfonamide carbonic anhydrase inhibitors (CAI) having the formula:

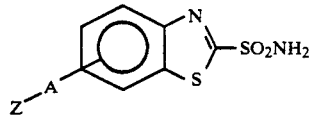

wherein Z is a water soluble carrier, and A is a moiety which when attached to said 2-benzothiazolesulfonamide will still retain CAI activity and which can also form an enzymatically cleavable bond with Z.

2. The prodrugs of claim 1 wherein the water soluble carrier Z is selected from the group consisting of monosaccharides and 6-carboxylic acid derivatives of monosaccharides.

3. The prodrugs of claim 1 wherein A is selected from the group consisting of hydroxyethoxy, hydroxy, hydroxyacetamido, and amino.

4. The prodrugs of claim 1 wherein the enzymatically cleavable bond between Z and A is selected from the group consisting of ester, glycosidic, carbonate, carbamate, thiocarbamate, urea, and thiourea bonds.

5. The prodrug of claim 4 wherein Z is a monosaccharide and the linkage is glycosidic.

6. The prodrug of claim 4 wherein Z is 6-carboxylic acid and the linkage is esteratic.

7. Prodrugs of hydroxymethazolamide carbonic anhydrase inhibitors (CAI) having the formula:

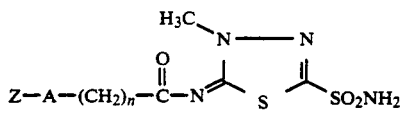

wherein n is from one to three, Z is a water soluble carrier, and A is a moiety which when attached to said hydroxymethazolamide which still retain CAI activity and which can also form an enzymatically cleavable bond with Z.

8. The prodrugs of claim 7 wherein the water soluble carrier Z is selected from the group consisting of monosaccharides and 6-carboxylic acid derivatives of monosaccharides.

9. The prodrugs of claim 7 wherein A is selected from the group consisting of hydroxyethoxy, hydroxy, hydroxyacetamido, and amino.

10. The prodrugs of claim 7 wherein the enzymatically cleavable bond between Z and A is selected from the group consisting of ester, glycosidic, carbonate, carbamate, thiocarbamate, urea, and thiourea bonds.

11. The prodrug of claim 10 wherein Z is a monosaccharide and the linkage is glycosidic.

12. The prodrug of claim 10 wherein Z is 6-carboxylic acid and the linkage is esteratic.

13. Prodrugs of dichlorphenamide carbonic anhydrase inhibitors (CAI) having the formula:

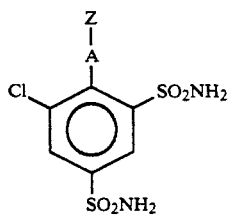

wherein Z is a water soluble carrier, and A is a moiety which when attached to said dichlorphenamide will still retain CAI activity and which can also form an enzymatically cleavable bond with Z.

14. The prodrugs of claim 13 wherein the water soluble carrier Z is selected from the group consisting of monosaccharides and 6-carboxylic acid derivatives of monosaccharides.

15. The prodrugs of claim 13 wherein A is selected from the group consisting of hydroxyethoxy, hydroxy, hydroxyacetamido, and amino.

16. The prodrugs of claim 13 wherein the enzymatically cleavable bond between Z and A is selected from the group consisting of ester, glycosidic, carbonate, carbamate, thiocarbamate, urea, and thiourea bonds.

17. The prodrug of claim 16 wherein Z is a monosaccharide and the linkage is glycosidic.

18. The prodrug of claim 16 wherein Z is 6-carboxylic acid and the linkage is esteratic.

19. A method of reducing intraocular eye pressure, said method comprising:
(a) topically applying to the eye a small but therapeutically effective intraocular eye pressure reducing amount of a prodrug of 2-benzothiazolesulfonamide carbonic anhydrase inhibitor having the formula:

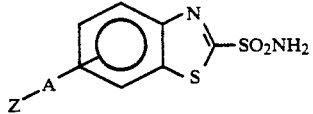

wherein Z is a water soluble carrier, and A is a moiety which when attached to said 2-benzothiazolesulfonamide will still retain CAI activity and which can also form an enzymatically cleavable bond with Z.

20. A method of reducing intraocular eye pressure, said method comprising:
(a) topically applying to the eye a small but therapeutically effective intraocular eye pressure reducing amount of a prodrug of hydroxymethazolamide carbonic anhydrase inhibitor having the formula:

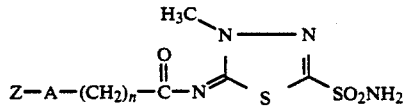

wherein n is from one to three, Z is a water soluble carrier, and A is a moiety which when attached to said hydroxymethazolamide will still retain CAI activity and which can also form an enzymatically cleavable bond with Z.

21. A method of reducing intraocular eye pressure, said method comprising:
(a) topically applying to the eye a small but therapeutically effective intraocular eye pressure reducing amount of a prodrug of dichlorphenamide carbonic anhydrase inhibitor having the formula:

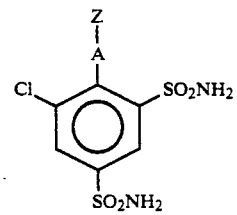

wherein Z is a water soluble carrier, and A is a moiety which when attached to said dichlorphenamide will still retain CAI activity and which can also form an enzymatically cleavable bond with Z.

22. A topical composition for eye drop treatment, comprising:
a small but therapeutically effective intraocular eye pressure reducing amount of an analog of 2-benzothiazolesulfonamide carbonic anhydrase inhibitor of the formula:

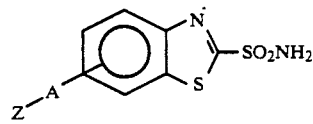

wherein Z is a water soluble carrier, and A is a moiety which when attached to said 2-benzothiazolesulfonamide will still retain CAI activity and which can also form an enzymatically cleavable bond with Z and an opthalmically acceptable carrier.

23. A topical composition for eye drop treatment, comprising:
a small but therapeutically effective intraocular eye pressure reducing amount of an analog of hyroxymethazolamide carbonic anhydrase inhibitor of the formula:

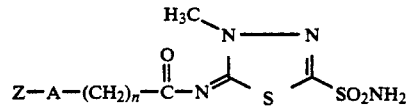

wherein n is from one to three, Z is a water soluble carrier, and A is a moiety which when attached to said hydroxymethazolamide will still retain CAI activity and which can also form an enzymatically cleavable bond with Z and an opthalmically acceptable carrier.

24. A topical composition for eye drop treatment, comprising:
a small but therapeutically effective intraocular eye pressure reducing amount of an analog of dichlorphenamide carbonic anhydrase inhibitor of the formula:

$$\underset{\underset{SO_2NH_2}{\overset{Cl}{\bigcirc}}}{\overset{Z}{\underset{|}{\overset{|}{A}}}}\ SO_2NH_2$$

wherein Z is a water soluble carrier, and A is a moiety which when attached to said dichlorphenamide will still retain CAI activity and which can also form an enzymatically cleavable bond with Z and an opthalmically acceptable carrier.

* * * * *